United States Patent [19]

Ashimori et al.

[11] Patent Number: 4,886,819
[45] Date of Patent: Dec. 12, 1989

[54] DIHYDROPYRIDINE DERIVATIVES AND PHARMACEUTICAL COMPOSITION THEREOF

[75] Inventors: Atsuyuki Ashimori; Taizo Ono; Yoshihisa Inoue, all of Kyoto; Chikara Fukaya; Kazumasa Yokoyama, both of Osaka, all of Japan

[73] Assignee: The Green Cross Corporation, Higashi, Japan

[21] Appl. No.: 87,513

[22] Filed: Aug. 20, 1987

[30] Foreign Application Priority Data

Aug. 27, 1986 [JP] Japan .................................. 61-200849
Oct. 23, 1986 [JP] Japan .................................. 61-253077
May 12, 1987 [JP] Japan .................................. 62-115590

[51] Int. Cl.$^4$ .................. C07D 211/86; A61K 31/455
[52] U.S. Cl. ..................................... 514/356; 514/252; 514/255; 514/332; 514/334; 546/321; 546/257; 546/261; 546/262; 546/265; 544/364; 544/365
[58] Field of Search ............... 546/321, 257, 261, 262, 546/265; 544/365, 364; 514/252, 255, 332, 334, 356

[56] References Cited

U.S. PATENT DOCUMENTS

| | | | |
|---|---|---|---|
| 4,510,310 | 4/1985 | Wehinger | 546/321 |
| 4,595,690 | 6/1986 | Clark et al. | 546/321 |
| 4,603,135 | 7/1986 | Meguro et al. | 546/321 |
| 4,618,607 | 10/1986 | Araki | 514/212 |
| 4,656,181 | 4/1987 | Sunkel et al. | 546/321 |
| 4,686,222 | 8/1987 | Atkinson | 514/255 |

FOREIGN PATENT DOCUMENTS

| | | |
|---|---|---|
| 0026317 | 4/1981 | European Pat. Off. |
| 0088903 | 9/1983 | European Pat. Off. |
| 0097821 | 1/1984 | European Pat. Off. |
| 0191448 | 8/1986 | European Pat. Off. |
| 2935451 | 3/1981 | Fed. Rep. of Germany |

OTHER PUBLICATIONS

Chem. Abstr., vol. 105, No. 13, 114923v (Clark).
Chem. Abstr., vol. 36, No. 5, 29638a (Bossert).
Chem. Abstr., vol. 106, No. 5, 32844G (Clark); 32841y (Poindexter).

Primary Examiner—Jane T. Fan
Attorney, Agent, or Firm—Berman, Aisenberg & Platt

[57] ABSTRACT

Dihydropyridine derivatives of the formula

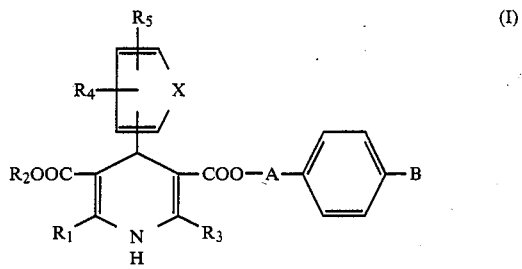

wherein $R_1$, $R_2$, $R_3$, $R_4$, $R_5$, A, B are defined as in the specification and nontoxic acid-addition salts thereof, have an excellent calcium blocking action (Ca-antagonist), and antihypertensive action, a platelet aggregation-inhibiting action, a phosphodiesterase-inhibiting action and the like, and thus are useful as a medicine, such as a coronary vasocilator, a cerebral hyperkinemic, antihypertensive, thrombosis-preventing or -treating agents, phosphodiesterase-inhibitor or the like. Pharmaceutical compositions and methods of use are also disclosed.

15 Claims, No Drawings

DIHYDROPYRIDINE DERIVATIVES AND PHARMACEUTICAL COMPOSITION THEREOF

FIELD OF THE INVENTION

This invention relates to dihydropyridine derivatives and acid-addition salts thereof which are novel and useful as pharmaceuticals, and pharmaceutical composition thereof.

BACKGROUND OF THE INVENTION

As compounds similar to dihydropyridine derivatives of the present invention, there have been known, for example, nifedipine, nicardipine, etc. While these compounds have been known to be useful as an antihypertensive agent, a peripheral and cerebral vasodilating agent and a coronary artery-treating (angina pectoris-treating) agent, it has been demanded that dihydropyridine derivatives having still more excellent effect are presented.

SUMMARY OF THE INVENTION

The object of the present invention is to provide dihydropyridine derivatives and acid-addition salts thereof which have still more excellent pharmacological activities.

DETAILED DESCRIPTION OF THE INVENTION

This invention relates to dihydropyridine derivatives represented by the formula (I)

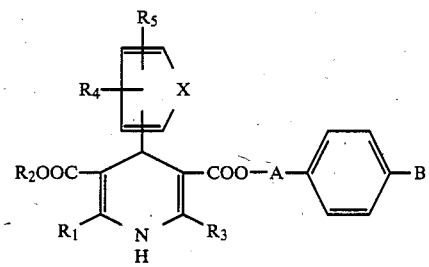

wherein $R_1$, $R_2$ and $R_3$ are the same or different and each is alkyl, cycloalkyl or alkoxyalkyl; $R_4$ and $R_5$ are the same or different and each is a hydrogen atom, halogen, nitro, halogenated alkyl, alkylsulfonyl, halogenated alkoxy, alkylsulfinyl, alkyl, cycloalkyl, alkoxy, cyano, alkoxycarbonyl or alkylthio (where both of $R_4$ and $R_5$ are not hydrogen atoms at the same time); X is a group represented by vinylene or azomethine; A is alkylene; and B is a group of the formula $-N(R_6)_2$ or

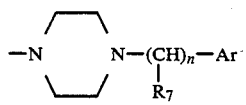

(wherein $R_6$ and $R_7$ are, independently, a hydrogen atom, alkyl, cycloalkyl, aralkyl, aryl or pyridyl, Ar is aryl or pyridyl, and n is an integer of 0 to 2) [hereinafter referred to briefly as dihydropyridine derivatives (I)], and nontoxic acid-addition salts thereof, which have an excellent calcium blocking action (Ca-antagonist), an antihypertensive action, a platelet aggregation-inhibiting action, a phosphodiesterase-inhibiting action and the like, and thus are useful as a medicine, such as a coronary vasodilator, a cerebral hyperkinemic; antihypertensive, thrombosis-preventing or -treating agents, phosphodiesterase-inhibitor or the like.

The dihydropyridine derivative (I) of the present invention has a unique structure as compared with dihydropyridine compounds which have been so far concretely known, and has a specific activity due to the unique structure. Namely, the dihydropyridine derivatives (I) of the present invention and their acid-addition salts are characterized remarkably in that they show a high organ and tissue-selectivity in vasodilating activities particularly and that they are very low in acute toxicity and thus highly safe.

In the above formula, the alkyl represented by $R_1$, $R_2$ and $R_3$ may be straight or branched, and particularly a lower alkyl ($C_{1-6}$), such as methyl, ethyl, propyl, isopropyl, butyl, isobutyl, sec-butyl, t-butyl, pentyl, isopentyl, neopentyl, hexyl, etc, is preferable; and $C_{1-4}$ alkyls are preferred. The alkyl may have at the terminus a lower cycloalkyl ($C_{3-6}$) (e.g. cyclopropylmethyl, cyclobutylethyl, cyclopentylmethyl). As the cycloalkyl, preferred is a lower ($C_{3-6}$) cycloalkyl, such as cyclopropyl, cyclobutyl, cyclopentyl and cyclohexyl. As the alkoxyalkyl, preferred is an alkoxyalkyl having 3 to 7 carbon atoms in total in the moiety, such as methoxyethyl, ethoxyethyl, propoxyethyl, isopropoxyethyl, butoxyethyl, methoxypropyl, 2-methoxy-1-methylethyl, 2-ethoxy-1-methylethyl, etc.

The substituents represented by $R_4$ and $R_5$ may be the same or different, and they may be attached to the ring at any position. Preferably, they are attached to the ring at the 2- and/or 3-positions relative to the position at which the dihydropyridine ring bonds to the ring. The halogen represented by $R_4$ and $R_5$ includes a fluorine atom, chlorine atom, a bromine atom and an iodine atom, among which fluorine and chlorine atoms are particularly preferable. As the alkyl and cycloalkyl represented by $R_4$ and $R_5$, preferred are the alkyls and cycloalkyls which are mentioned above as the examples for $R_1$ to $R_3$. As the alkoxy and alkylthio, preferred are alkoxys and alkylthios having a lower alkyl ($C_{1-3}$), which are exemplified by methoxy, ethoxy, propoxy and isopropoxy, and methylthio, ethylthio, propylthio and isopropylthio, respectively. As the alkoxycarbonyl, there can be mentioned those having 2 to 4 carbon atoms, such as methoxycarbonyl and ethoxycarbonyl. As the halogens of the halogenides, there are mentioned such halogens as mentioned above. The halogenated alkyls include those in which a part of the hydrogen atoms are halogenated [e.g. $(CF_3)_2CHCH_2-$, $CF_3CH_2$] and those in which all the hydrogen atoms are halogenated (e.g. trifluoromethyl). The alkyl moiety of the halogenated alkyl has preferably 1 to 4 carbon atoms. The halogenated alkoxys also include those in which a part of the hydrogen atoms are halogenated and those in which all the hydrogen atoms are halogenated. The alkyl moiety of the halogenated alkoxy preferably contains 1 to 3 carbon atoms. As the alkyl in the alkylsulfonyl and the alkylsulfinyl, there may be mentioned the alkyls which are mentioned above as the examples for $R_1$ to $R_3$.

As $R_4$ and $R_5$, particularly preferred are cyano and halogenated alkyls (particularly, trifluoromethyl).

As the alkyl and cycloalkyl represented by $R_6$ and $R_7$, there can be mentioned the alkyls and the cycloalkyls which are mentioned above as the examples for $R_1$ to $R_3$. As the aralkyl, there can be mentioned phenyl $C_{1-3}$- alkyl, such as benzyl, α-phenylethyl, β-phenylethyl and γ-phenylpropyl, and as the aryl, phenyl and naphthyl can be mentioned. The aromatic ring of them may have the same or different substituents at optional position of the ring. As the substituent on the aromatic ring, there may be mentioned, for example, those which are mentioned above as the examples for $R_4$ and $R_5$. The pyridyl includes 2-pyridyl, 3-pyridyl and 4-pyridyl, which may be substituted by the groups mentioned as the examples for $R_4$ and $R_5$.

As the alkylene represented by A, preferable are those having 2 to 4 carbon atoms and they may be straight or branched. They are exemplified by ethylene, trimethylene, tetramethylene, 1,2-dimethylethylene, etc.

The aryl and pyridyl represented by Ar include, for example, those which are mentioned above as the examples for $R_6$, and they may have the same substituents as the aryl and pyridyl represented by $R_6$.

The ring represented by the formula

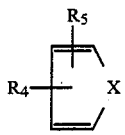

as the substituent at the 4-position of dihydropyridine means a benzene ring in case where X is vinylene (—CH=CH—), and a pyridine in case where X is azomethine (—CH=N—), and the ring may bind to the 4-position of the dihydropyridine at the optional position of itself.

The substituents represented by $R_4$ and $R_5$ may be attached to the ring at any of the ortho-, metha- and para-positions relative to the carbon atom binding to the 4-position of the dihydropyridine, and are attached preferably to the ortho- and/or meta-positions of the ring.

The dihydropyridine derivatives (I) can be produced by reacting a compound containing the optional constituent moiety of the said dihydropyridine derivatives (I) and the compounds containing the remaining constituent moiety thereof by a per se known means, particularly by subjecting them to dehydration ring-closure reaction. For example, the objective compounds can be produced in the following manner.

Production Method

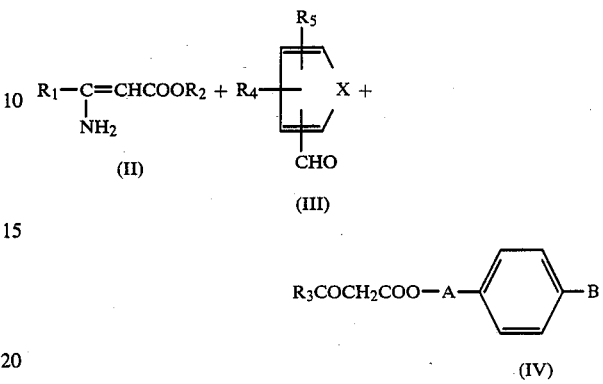

In the scheme, $R_1$, $R_2$, $R_3$, $R_4$, $R_5$, X, A and B have the same meanings as defined above.

The reaction of compounds (II), (III) and (IV) are usually carried out at temperatures ranging from about 20° C. to about 160° C., preferably from about 30° C. to about 130° C. As the solvent, any solvent can be used so long as it is inert to the reaction. Suitable solvents include, for example, alkanols, such as methanol, ethanol, propanol, isopropanol, butanol; sec-butanol, ethers, such as ethyl ether, dioxane, tetrahydrofuran, ethylene glycol monomethyl ether, ethylene glycol dimethyl ether,; acetic acid; pyridine; N,N-dimethylformamide, dimethylsulfoxide,; acetonitrile; etc. As for the amount of compounds (II), (III) and (IV) to be used, based on 1 mol of one of the three compounds, 1 to 1.5 mol of the other two compounds are usually used. The reaction is usually completed in about 1 to 30 hours.

Dihydropyridine derivatives (I) can be produced by the method or a method similar to the one disclosed in European Patent Publication No. 94159.

The main starting compound (IV) of the present invention can be synthesized, for example, by the following route.

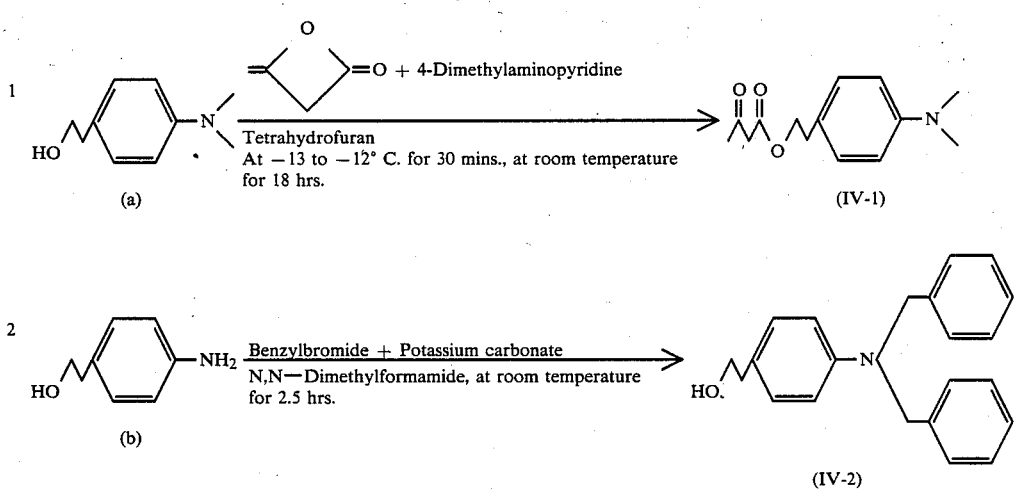

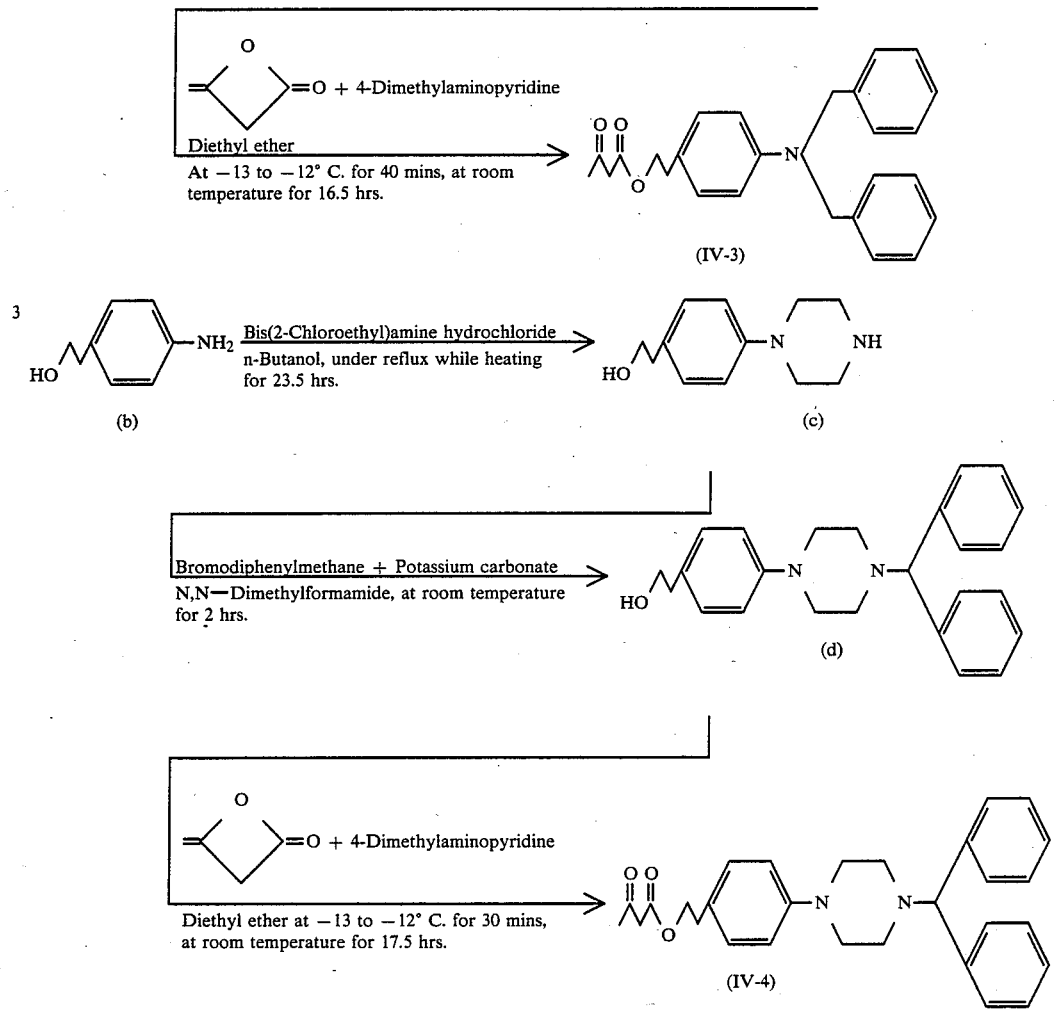

The compound (IV), including the compound (IV-1), (IV-2), (IV-3) and (IV-4), and compounds (c) and (d), etc., are used as starting materials in the production of the dihydropyridine derivatives (I); these compounds can be summarized by the following formula

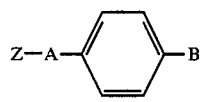

(A)

wherein Z is hydroxyl or the group represented by the formula $R_3$—CO—CH$_2$—COO—

$R_3$ is alkyl, cycloalkyl or alkoxyalkyl; A is alkylene., and B is a group of the formula —N(R$_6$)$_2$ or

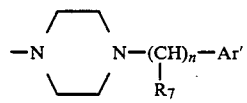

(wherein $R_6$ and $R_7$ are independently hydrogen atom, alkyl, cycloalkyl, aralkyl, aryl or pyridyl, Ar' is hydro- gen atom, aryl or pyridyl and n is an integer of 0 to 2) with the proviso that when Z is hydroxyl, $R_6$ is other than hydrogen atom or alkyl [hereinafter referred to briefly as compound (A)].

The compound (A) is generally produced by the methods described as follows.

Method (i):

The compound wherein Z is hydroxyl and B is —N(R$_6$)$_2$, namely the compound (A-1)

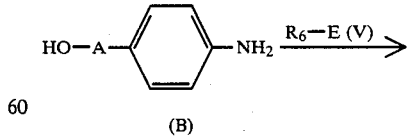

(B)

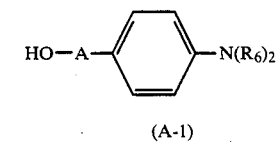

(A-1)

wherein A and $R_6$ are as defined above, and E is halogen atom.

The compound (A-1) of the present invention can be obtained by the reaction of compound (B) with compound (V). This reaction is carried out in the presence of an inert solvent (e.g. N,N-dimethylformamide (DMF), dimethylsulfoxide, diglyme, ethylene glycol monomethyl ether) for 1-5 hours at 10°-120° C. It is favorable that the reaction be conducted in the presence of alkali, such as potassium carbonate.

Method (ii):

The compound wherein Z is hydroxyl, B is

namely the compound (A-2); and the compound wherein Z is hydroxyl and B is

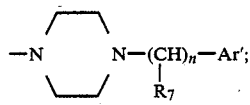

namely the compound (A-3)

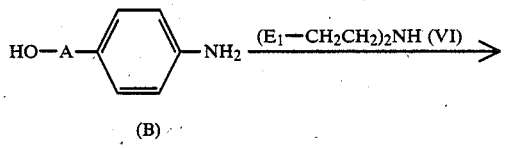

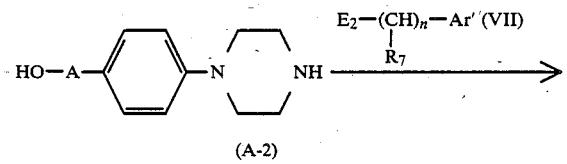

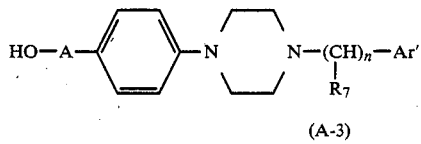

wherein A, Ar', $R_7$ and n are as defined above, and $E_1$ and $E_2$ respectively show halogen atom.

The compound (A-2) is obtained by reacting compound (B) with compound (VI). The present reaction can be carried out through reflux under heating for 20 to 30 hours in the presence of an inert solvent (e.g. n-butanol, sec-butanol, propanol).

Then, the compound (A-3) of the present invention can be obtained by reacting compound (A-2) with compound (VII). The condition of the present reaction is similar to that in Method (i).

Method (iii):

The compound wherein Z is $R_3$—CO—CH$_2$—COO—, namely the compound (A-4)

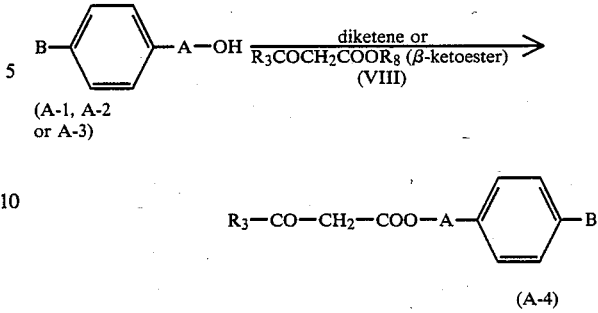

wherein $R_8$ represents a lower alkyl (usually $C_{1-4}$) and all the other symbols are as defined above.

That is, the compound (A-4) is produced by reacting compound (A-1), (A-2) or (A-3) with diketene or compound (VIII).

The reaction of compound (A-1), (A-2) or (A-3) with diketene is conducted by heating a mixture of the both compounds at about 40° C. to about 130° C. without any solvent or in a solvent inert to the reaction; or, it can also be carried out in the presence of a catalyst, such as p-di-methylaminopyridine, at about −20° C. to about 40° C. in a solvent inert to the reaction (e.g. dimethyl ether, tetrahydrofuran, dimethoxyethane).

Also, the compound (A-4) of the present invention can be produced by reacting compound (A-1), (A-2) or (A-3) with compound (VIII). This reaction is conducted in the presence of a base (e.g. sodium methoxide, sodium ethoxide, potassium t-butoxide, sodium hydride, sodium amide, metal sodium) at about 20° C. to about 100° C. in an inert solvent or without solvent.

The novel dihydropyridine derivatives (I) thus produced can be purified to an optional extent by a suitable known separation and purification means, such as concentration, extraction, chromatography, reprecipitation, or recrystallization.

Besides, since the dihydropyridine derivatives (I) have basic groups, they can be converted into acid-addition salts thereof by a known means. As for such salts, there is no limitation so long as they are pharmacologically acceptable nontoxic salts, as are exemplified by salts with inorganic acids (e.g. hydrochloride, hydrobromide, phosphate, sulfate) and those with organic acids (e.g. acetate, succinate, maleate, fumarate, malate, tartrate).

The dihydropyridine derivatives (I) and acid-addition salts thereof are extremely low in toxicity and have an antihypertensive action, a peripheral vasodilating action, a coronary artery-dilating action, a cerebral vasodilating action and other actions which are potent and lasting in mammals (e.g. mouse, rat, rabbit, dog, cat, man). Thus, they are useful as a medicine for prophylaxis and treatment of circulatory diseases, such as hypertension, ischemic cardiac diseases (angina pectoris, myocardial infarction etc.), cerebral and peripheral circulation disturbances (cerebral infarction, temporary cerebral ischemic spasm, etc.) and the like.

In particular, the dihydropyridine derivatives (I) and acid-addition salts thereof are superior in their potency and duration of pharmacological actions as compared with previously known dihydropyridine derivatives (e.g. nifedipine, nicardipine). Thus, for example, when they are used as a medicine for prophylaxis or treatment of hypertension, they give a stable antihypertensive action by a fewer times' dosage (once or twice a day).

When the dihydropyridine derivatives (I) and their acid-addition salts are used as medicines mentioned above, they can be mixed with pharmaceutically required ingredients, such as pharmacologically-acceptable, appropriate additives (e.g. carrier, excipient, diluent) to give a pharmaceutical composition in a form, such as powders, granules, tablets, capsules or injection, which can be orally or parenterally administered. The dihydropyridine derivatives (I) and their acid-addition salts are incorporated in the above-mentioned pharmaceutical compositions in a pharmaceutically-effective amount. While the dosage varies depending upon the administration route, severity of the diseases, the body weight or age of the patient, or the like, when they are orally administered to an adult patient suffering from hypertension, for example, they can be administered in an amount of 0.05 to 20 mg/kg body weight/day, preferably 0.1 to 4 mg/kg body weight/day in one to several divided doses a day.

EXPERIMENTAL EXAMPLE

The results of the pharmacological tests showing the effectivity of the dihydropyridine derivatives (I) and acid-addition salts thereof of the present invention are given below.

(1) Antihypertensive Action

The experiments were conducted with the use of male rats (three to five rats per a group) 10 to 11 weeks old and suffering from spontaneous hypertension. For blood pressure determination, systolic pressure was measured without anesthesia by an indirect tail-cuff method using a sphygmomanometer (PE-300, Narco Bio-System).

The test compounds were respectively suspended in 10% HCO-60 [general name: polyoxyethylene hardened castor oil, manufactured by Nikko Chemicals Corporation (Japan)] and the suspensions were orally administered in an amount of 25 mg/kg. After the administration, the blood pressure was measured with the lapse of time. The maximum ratio of decrease in the blood pressure (%) of the said compounds ranged from 4 to 33%. The period of time during which the decreased blood pressure value took to recover to the level of 50% of the blood pressure value before the administration was within the range of 5 to 17 hours.

(2) Acute Toxicity

The $LD_{50}$ was estimated with the use of male mice (3 to 5 mice per a group) at the age of 10 to 11 weeks, weighing 14–16 g. The results were at least more than 1100 mg/Kg and those of most test compounds were more than 1400 mg/Kg.

Accordingly, the compounds which the present invention provides are significantly lower in their acute toxicity than known compounds and thus safer.

The present invention is explained in further detail by illustrating below working examples, which are not to be construed to be limitative of the present invention.

In $^1$H-NMR measurement, unless otherwise specified, $CDCl_3$ was used.

EXAMPLE 1

(1) 2-(p-Dimethylaminophenyl)ethyl acetoacetate 2-(p-Dimethylaminophenyl)ethanol (3.131 g, 18.9 mmol) was put in a 200 ml-three-necked flask, which was equipped with an air condenser on the center mouth, a thermometer in one of the side mouths and a septum rubber in the other mouth. Tetrahydrofuran (THF) (59 ml) was added in the flask to dissolve the content, and the mixture was cooled to $-13°$ to $-12°$ C. (with ice-sodium chloride). Then, diketene (1.912 g, 22.7 mmol) and 4-dimethylaminopyridine (DMAP) (10 mg, 0.082 mmol) were added thereto. The mixture was stirred at the same temperature for 30 minutes and then at room temperature for 18 hours. After the reaction mixture was ice-cooled, a 0.1% aqueous solution of sodium hydroxide (75 ml) was added thereto. The reaction mixture was extracted with ethyl acetate (four times, 90 ml each time). The ethyl acetate layer was washed with a 0.1% aqueous solution of sodium hydroxide (once, 75 ml) and brine (twice, 50 ml each time), and dried. After distillation under reduced pressure, the residue (5.069 g) was subjected to column chromatography [silica gel, ethyl acetate-n-hexane (1:2)] for separation and purification to give 3.592 g of the subject acetoacetic acid ester (Yield: 76%).

$IR\nu_{max}^{KBr}cm^{-1}$: 1740(C=O), 1710(C=O)
$^1$H-NMR δ:
7.02, 6.63 (4H, $A_2B_2q$, J=9Hz),
4.27 (2H, t, J=7Hz),
3.38 (2H, s),
2.89 (6H, s),
2.84 (2H, t, J=7Hz),
2.20 (3H, s), (2) 2-(p-Dimethylaminophenyl)ethyl methyl 2,6-dimethyl-4-(4-cyano-2-pyridyl)-1,4-dihydropyridine-3,5-dicarboxylate (compound 1-1) and its monohydrochloride (compound 1-2)

In a 50 ml-pear-shaped flask were put 4-cyano-2-pyridine-aldehyde (1.005 g, 7.61 mmol), the objective compound of (1) (1.896 g, 7.60 mmol) and methyl 3-aminocrotonate (903 mg, 7.61 mmol), whereto isopropanol (10 ml) was added to dissolve the content. With a Dimroth condenser equipped on the flask, the mixture was stirred at 40° to 45° C. for 26 hours. The reaction solvent was distilled off under reduced pressure. The residue (3.668 g) was subjected to column chromatography [silica gel, ethyl acetate-n-hexane (9:1)] for separation to give a crude product. This crude product was recrystallized from methanol to give 1.576 g of the above-captioned compound 1-1 (Yield: 45%). m.p. (what was recrystallized from methanol): 184°–186° C.

$IR\nu_{max}^{KBr}cm^{-1}$: 2225(CN), 1705(C=O), 1665(C=O)
$^1$H-NMR δ:
8.52 (1H, d, J=5Hz),
7.4–7.15 (2H),
7.05 (1H, s),
7.00, 6.62 (4H, $A_2B_2q$, J=8Hz),
5.14 (1H, s),
4.24 (2H, t, J=6Hz),
3.63 (3H, s),
2.91 (6H, s),
2.80 (2H, t, J=6Hz),
2.25 (6H, s)

This compound 1-1 (1.428 g, 3.10 mmol) was put in a 100 ml-three-necked flask, which was equipped with a Dimooth condenser on the central mouth and septum rubbers on the side mouths. In the flask, methylene chloride (40 ml) was added to dissolve the content, and a dioxane solution of hydrogen chloride (2.49N, 1.244 ml) was added. The mixture was stirred at room temperature for two hours. The resulting crystals were subjected to suction filtration and washed with methylene chloride (40 ml) to give about 1.26 g of the hydrochloride (compound 1-2).

IR$\nu_{max}^{KBr}$ cm$^{-1}$: 2425 (→N$^+$H$^-$Cl),
2225(CN), 1690(C=0), 1665(C=0)
$^1$H-NMR δ DMSO-d6+CDCl3(2:1.5):
8.90 (1H, s),
8.62 (1H, d, J=5 Hz),
7.8-7.15 (6H),
5.06 (1H, s),
4.21 (2H, t, J=6 Hz),
3.58 (3H, s),
3.12 (6H, s),
2.90 (2H, t, J=6 Hz),
2.28, 2.22 (each 3H, s)

(3) 2-(p-Dimethylaminophenyl)ethyl methyl 2,6-dimethyl-4-(2-trifluoromethyl-3-pyridyl)-1,4-dihydropyridine-3,5-dicarboxylate (compound 2-1) and its monohydrochloride (compound 2-2)

In a 50 ml-pear-shaped flask were put 2-trifluoromethyl-3-pyridine aldehyde (1.023 g, 5.84 mmol), the objective compound of (1) (1.438 g, 5.77 mmol) and methyl 3-aminocrotonate (685 mg, 5.77 mmol), whereto isopropanol (10 ml) was added to dissolve the content. After a Dimorth condenser was equipped, the mixture was stirred at 40° to 45° C. for 45.5 hours. After the reaction solvent was distilled off under reduced pressure, the residue (3.244 g) was subjected to column chromatography [silica gel, ethyl acetate-n-hexane (2:1)] for separation to give a crude product, and it was recrystallized from methanol to give 1.277 g of the compound 2-1 (Yield: 43%) m.p. (what was recrystallized from methanol): 199°–204° C.

IR$\nu_{max}^{KBr}$ cm$^{-1}$: 1710(C=0), 1695(C=0)
$^1$H-NMR δ:
8.55-8.4 (1H),
8.05-7.8 (1H),
7.5-7.25 (1H),
7.15-6.9 (2H),
6.75-6.5 (2H),
6.01 (1H, s)
5.63 (1H, s),
4.16 (2H, t, J=7Hz),
3.58 (3H, s),
2.89 (6H, s),
2.75 (2H, t, J=7Hz),
2.30, 2.27 (each 3H, s)

The compound 2-1 (1.180 g, 2.34 mmol) was put in a 100 ml-three-necked flask, which was equipped with an air condenser on the central mouth and septum rubbers on the side mouths. After methylene chloride (30 ml) was added thereto to dissolve the content, a dioxane solution of hydrogen chloride (2.49N, 0.941 ml) was added. The mixture was stirred at room temperature for 2.5 hours. The reaction solvent was distilled off under reduced pressure. Ethanol (25 ml) was added to the residue and then the mixture was distilled off under reduced pressure to give about 1.26 g of the hydrochloride (compound 2-2).

IR$\nu_{max}^{KBr}$ cm$^{-1}$: 2625(→N$^+$H$^-$Cl), 1690(C=0)
$^1$H-NMR δ DMSO-d6+CDCl3(2:1.5):

-continued
8.94 (1H, s),
8.6-8.4 (1H,),
8.05-7.8 (1H),
7.75-7.4 (3H),
7.35-7.1 (2H),
5.43 (1H, s),
4.16 (2H, t, J=6Hz),
3.53 (3H, s),
3.15 (6H, s),
2.84 (2H, t, J=6Hz),
2.29, 2.24 (each 3H, s)

EXAMPLE 2

(1) 2-(p-Dibenzylaminophenyl)ethanol 2-(p-Aminophenyl)ethanol (1.041 g, 7.59 mmol) was put in a 50 ml-three-necked flask, which was equipped with a Dimroth condenser on the central mouth and septum rubbers on the side mouths. In the flask, N,N-dimethylformamide (DMF) (8.6 ml) was added to dissolve the content, and potassium carbonate (4.195 g, 30.4 mmol) and benzyl bromide (2.985 g, 17.5 mmol) were added. The mixture was stirred at room temperature for 2.5 hours. Water (40 ml) was added to the reaction mixture, and the mixture was extracted with diethyl ether (four times, 40 ml each time). The ether layer was washed with brine (once, 25 ml), dried, and distilled off under reduced pressure. The obtained residue (3.042 g) was subjected to column chromatography [silica gel, chloroform methanol (98:2)] for separation and purification to give 2.275 g of the above-captioned compound (Yield: 94%)

IR$\nu_{max}^{neat}$ cm$^{-1}$: 3350(OH)
$^1$H-NMR δ:
7.18 (10H, s),
6.92, 6.62 (4H, A$_2$B$_2$q, J=8.5Hz),
4.56(4H, s),
3.71 (2H, t, J=6Hz),
2.69 (2H, t, J=6Hz),
1.48 (1H, s)

(2) 2-(p-Dibenzylaminophenyl)ethyl acetoacetate 2-(p-Dibenzylaminophenyl)ethanol (7.020 g, 22.1 mmol) was put in a 200 ml-three-necked flask, which was equipped with an air condenser on the central mouth, a thermometer on one of the side mouths and a septum rubber on the other mouth. In the flask, diethyl ether (68 ml) was added to dissolve the content, and the solution was cooled to −13° to −12° C. (with ice and sodium chloride). To the solution, diketene (2.113 g, 25.1 mmol) and DMAP (9 mg, 0.074 mmol) were added. The mixture was stirred at the same temperature for 40 minutes and at room temperature for 16.5 hours. The reaction mixture was washed by adding it to a 0.1% ice-cooled aqueous solution of sodium hydroxide (90 ml) in a 300 ml-conical flask. The mixture was separated into a diethyl ether layer and a water layer. The water layer was extracted with ether (three times, 110 ml each time). The extract was combined with the diethyl ether layer, washed with a 0.1% aqueous solution of sodium hydroxide (twice, 90 ml each time) and then with brine (twice, 50 ml each time), dried, and distilled off under reduced pressure. The residue (7.972 g) was subjected to column chromatography [silica gel, ethyl acetate-n-hexane (1:3)] for separation and purification to give 7.266 g of the above-captioned acetoacetic acid ester (Yield: 82%).

IR$\nu_{max}^{neat}$cm$^{-1}$: 1740(C=O), 1720(C=O)
$^1$H-NMR$\delta$:
7.19 (10H, s),
7.1-6.8 (2H),
6.75-6.5 (2H),
4.57 (4H, s),
4.25 (2H, t, J=6Hz),
3.36 (2H, s),
2.81 (2H, t, J=6Hz),
2.15 (3H, s)

(3) 2-(p-Dibenzylaminophenyl)ethyl methyl 2,6-dimethyl-4-(4-cyano-2-pyridyl)-1,4-dihydropyridine-3,5-dicarboxylate (compound 3-1) and its mono hydrochloride (compound 3-2)

In a 50 ml-pear-shaped flask were put 4-cyano-2-pyridinealdehyde (1.032 g, 7.81 mmol), the objective compound of (2) (3.136 g, 7.81 mmol) and methyl 3-aminocrotonate (927 mg, 7.81 mmol), and isopropanol (10 ml) was added to dissolve the content. With a Dimroth condenser equipped on the mouth of the flask, the mixture was stirred at 40° to 45° C. for 20 hours. The reaction solvent was distilled off under reduced pressure. The residue (5.1 g) was subjected to column chromatography [silica gel, ethyl acetate-n-hexane (2:1)] and [silica gel, chloroform-methanol (98.5:1.5)] for separation to give a crude product, and it was recrystallized from methanol-chloroform to give 1.924 g of the compound 3-1 (Yield: 40%). m.p. (what was recrystallized from methanol-chloroform): 194.5°-197° C.

IR$\nu_{max}^{KBr}$cm$^{-1}$: 2225(CN), 1700(C=O), 1660(C=O)
$^1$H-NMR$\delta$:
8.50 (1H, d, J=5Hz),
7.45-7.05 (12H),
7.05-6.8 (3H),
6.75-6.5 (2H),
5.17 (1H, s),
4.58 (4H, s),
4.18 (2H, t, J=6Hz),
3.55 (3H, s),
2.74 (2H, t, J=6Hz),
2.24, 2.19 (each 3H, s)

The compound 3-1 (1.807 g, 2.95 mmol) was put in a 100 ml-three-necked flask, which was equipped with an air condenser on the central mouth and septum rubbers on the side mouths. In the flask, methylene chloride (38 ml) was added to dissolve the content, and a dioxane solution of hydrogen chloride (1.20N, 2.458 ml) was added. The mixture was stirred at room temperature for 1.5 hours. After the reaction solvent was distilled off under reduced pressure, ethanol (30 ml) was added to the residue, and the mixture was distilled off under reduced pressure to give about 1.91 g of the hydrochloride (compound 3-2).

IR$\nu_{max}^{KBr}$cm$^{-1}$: 2250(→N$^+$H$^-$Cl), 2250(CN), 1680(C=O)
$^1$H-NMR$\delta$:
8.8-8.6 (1H),
7.8-7.6 (2H),
7.5-6.85 (11H),
5.24 (1H, s),
4.69 (4H, s),
4.16 (2H, t, J=6Hz),
3.61 (3H, s),
2.76 (2H, t, J=6Hz),
2.39, 2.28 (each 3H, s)

(4) 2-(p-Dibenzylaminophenyl)ethyl methyl 2,6-dimethyl-4-(2-trifluoromethyl-3-pyridyl)-1,4-dihydropyridine-3,5-dicarboxylate (compound 4-1) and its monohydrochloride (compound 4-2)

In a 50 ml-pear-shaped type flask were put 2-trifluoromethyl-3-pyridinealdehyde (1.099 g, 6.28 mmol), the objective compound of (2) (2.376 g, 5.92 mmol) and methyl 3-aminocrotonate (702 mg, 5.91 mmol), and isopropanol (7.6 ml) was added to dissolve the content. With a Dimroth condenser equipped on the flask, the mixture was stirred at 40° to 45° C. for 32 hours and then at room temperature for 40 hours. The residue (3.976 g) obtained by distilling off the reaction solvent was subjected to column chromatography [silica gel, ethyl acetate-n-hexane (1:1)] and [silica gel, chloroform-methanol (98:2)] for separation to give a crude product, and it was recrystallized from isopropyl ether-methanol-chloroform to give 1.436 g of the compound 4-1 (Yield: 37%). m.p. (what was recrystallized from isopropyl ether-methanol-chloroform): 141°-142° C.

IR$\nu_{max}^{KBr}$cm$^{-1}$: 1695(C=O)
$^1$H-NMR$\delta$:
8.5-8.3 (1H),
7.95-7.7 (1H),
7.4-7.1 (11H),
7.0-6.75 (2H),
6.7-6.5 (2H),
5.91 (1H, s),
5.60 (1H, s),
4.59 (4H, s),
4.15 (2H, t, J=6.5Hz),
3.56 (3H, s),
2.67 (2H, t, J=6.5Hz),
2.27, 2.21 (each 3H, s)

The compound 4-1 (1.212 g, 1.85 mmol) was put in a 100 ml-three-necked flask, which was equipped with an air condenser on the central mouth and septum rubbers on the side mouths. In the flask, methylene chloride (24 ml) was added to dissolve the content, and a dioxane solution of hydrogen chloride (1.20N, 1.540 ml) was added. The mixture was stirred at room temperature for 2.5 hours. After the reaction solvent was distilled off under reduced pressure, ethanol (20 ml) was added to the residue, and the mixture was distilled off under reduced pressure to give about 1.28 g of the hydrochloride (compound 4-2).

IR$\nu_{max}^{KBr}$cm$^{-1}$: 2500(→N$^+$H$^-$Cl), 1690(C=O)
$^1$H-NMR$\delta$:
8.5-8.3 (1H),
8.05-7.8 (1H),
7.55-7.05 (14H),
7.05-6.8 (2H),
5.66 (1H, s),
4.69 (4H, s),
4.45-3.9 (2H),
3.58 (3H, s),
2.95-2.55 (2H),
2.40, 2.31 (each 3H, s)

EXAMPLE 3

(1) 2-(p-Piperazinophenyl)ethanol

In a 200 ml-pear-shaped type flask were put 2-(p-aminophenyl)ethanol (10.153 g, 74.0 mmol) and bis(2-chloroethyl)amine hydrochloride (6.605 g, 37.0 mmol), whereto n-butanol (66 ml) was added. With a Dimroth condenser equipped, the mixture was refluxed under heating for 23.5 hours. After the reaction mixture was cooled to the neighborhood of room temperature, it was added to water (218 ml) in a 500 ml-beaker. Under ice-cooling, a 15% aqueous solution of sodium hydroxide was added to adjust to pH 10 to 11, and the mixture was extracted with chloroform (five times, 300 ml each time). The chloroform layer was washed with brine (twice, 150 ml each time) and dried. The residue (13.485 g) obtained by distillation under reduced pressure was subjected to column chromatography [silica gel, chloroform-methanol (1:1)] for separation and purification to give 5.996 g of the above-captioned piperazine compound (Yield: 79%).

$IR\nu_{max}^{KBr}cm^{-1}$: 3300(OH)
$^1$H-NMR$\delta$:
7.15–6.95 (2H),
6.95–6.7 (2H),
3.77 (2H, t, J=6Hz),
3.2–2.8 (8H),
2.75 (2H, t, J=6Hz),
2.10 (2H, s)

(2) 2-[p-(4-Benzhydrylpiperazino)phenyl] ethanol

The product of (1) (the piperazine compound) (5.996 g, 29.1 mmol) was put in a 100 ml-three-necked flask, which was equipped with a Dimroth condenser on the central mouth and septum rubbers on the side mouths. In the flask, DMF (33 ml) was added to dissolve the content, and potassium carbonate (8.034 g, 58.1 mmol) and bromodiphenylmethane (7.543 g, 30.5 mmol) were added. The mixture was stirred at room temperature for 2 hours. The reaction mixture was added to water (80 ml) in a 200 ml-conical flask, and the mixture was extracted with diethyl ether (four times, 100 ml each time). The ether layer was washed with brine (twice, 40 ml each time), dried and distilled off under reduced pressure. The residue (10.616 g) was subjected to column chromatography [silica gel, ethyl acetate-n-hexane (1:1)] for separation and purification to give 6.188 g of the above-captioned benzhydrylpiperazine compound (Yield: 57%).

$IR\nu_{max}^{CHCl_3}cm^{-1}$: 3600(OH)
$^1$H-NMR$\delta$:
7.55–6.9 (12H),
6.9–6.55 (2H),
4.23 (1H, s),
3.72 (2H, t, J=6Hz),
3.3–2.95 (4H),
2.95–2.35 (6H),
1.71 (1H, s)

(3) 2-[p-(4-Benzhydrylpiperazino)phenyl] ethyl acetoacetate

The product of (2) (the benzhydrylpiperazine compound) (5.970 g, 16.0 mmol) was put in a 200 ml-three-necked flask, which was equipped with an air condenser on the central mouth, a thermometer on one of the side mouths and a septum rubber on the other mouth. In the flask, diethyl ether (50 ml) was added to dissolve the content. After the mixture was cooled to −13° to −12° C. (with ice-sodium chloride), diketene (1.531 g, 18.2 mmol) and DMAP (7 mg, 0.057 mmol) were added thereto. The mixture was stirred at the same temperature for 30 minutes and then at room temperature for 17.5 hours. The reaction mixture was ice-cooled, washed by adding a 0.1% aqueous solution of sodium hydroxide (65 ml), and separated into a water layer and a diethyl ether layer. The water layer was extracted with ether (three times, 120 ml each time). The ether extract was combined with the said diethyl ether layer and it was washed with a 0.1% aqueous solution of sodium hydroxide (twice, 65 ml each time) and then with water (twice, 50 ml each time), dried, and was distilled off under reduced pressure to give 7.364 g of the above-captioned acetoacetic acid ester stoichiometrically.

$IR\nu_{max}^{neat}cm^{-1}$: 1740(C=O), 1720(C=O),
$^1$H-NMR$\delta$:
7.6–6.9 (12H),
6.9–6.65 (2H),
4.29 (2H, t, J=6.5Hz),
4.24 (1H, s),
3.39 (2H, s),
3.35–3.0 (4H),
2.85 (2H, t, J=6.5Hz),
2.7–2.4 (4H),
2.18 (3H, s)

(4) 2-[p-(4-benzhydrylpiperazino)phenyl] ethyl methyl 2,6-dimethyl-4-(4-cyano-2-pyridyl)-1,4-dihydropyridine-3,5-dicarboxylate (compound 5-1) and its monohydrochloride (compound 5-2)

In a 50 ml-pear-shaped flask were put 4-cyano-2-pyridinealdehyde (684 mg, 5.18 mmol), the objective compound of (3) (2.363 g, 5.18 mmol) and methyl 3-aminocrotonate (614 mg, 5.18 mmol), whereto isopropanol (7 ml) was added. With a Dimroth condenser equipped on the flask, the mixture was stirred at 40° to 45° C. for 26 hours. The reaction solvent was distilled off under reduced pressure, and the obtained residue (3.539 g) was subjected to column chromatography [silica gel, ethyl acetate-n-hexane (3:1)] and [silica gel, ethyl acetate-n-hexane (2:1)] for separation to give a crude product. The crude product was recrystallized from chloroform-methanol to give 1.649 g of the compound 5-1 (Yield: 48%). m.p. (what was recrystallized from chloroform-methanol): 218°–220° C.

$IR\nu_{max}^{KBr}cm^{-1}$: 2225(CN), 1700(C=O), 1665(C=O)
$^1$H-NMR$\delta$:
8.65–8.45 (1H),
7.6–6.65 (17H),
5.16 (1H, s),
4.4–4.0 (3H),
3.59 (3H, s),
3.3–2.95 (4H),
2.95–2.45 (6H),
2.25, 2.22 (each 3H, s)

The compound 5-1 (1.092 g, 1.64 mmol) was put in a 100 ml-three-necked flask, which was equipped with an air condenser on the central mouth and septum rubbers on the side mouths. In the flask, methylene chloride (21 ml) was added to dissolve the content, and a dioxane solution of hydrogen chloride (1.20N, 1.363 ml) was added. The mixture was stirred at room temperature for 5 hours. After the reaction solvent was distilled off under reduced pressure, ethanol (15 ml) was added to the residue, and the mixture was distilled off under reduced pressure to give about 1.15 g of the compound 5-2.

$IR\nu_{max}^{KBr}cm^{-1}$: 2225(CN), 1680(C=O)
$^1$H-NMRδ DMSO-d6+CDCl3(2:1.5):
8.74 (1H, s),
8.57 (1H, d, J=5Hz),
7.55–7.1 (12H),
7.1–6.6 (4H),
5.05 (1H, s),
4.35–3.95 (2H),
3.75–2.6 (14H),
2.25, 2.23 (each 3H, s)

(5) 2-[p-(4-Benzhydrylpiperazino)phenyl] ethyl methyl 2,6-dimethyl-4-(2-trifluoromethyl-3-pyridyl)-1,4-dihydropyridine-3,5-dicarboxylate (compound 6-1) and its monofumarate (compound 6-2)

2-Trifluoromethyl-3-pyridinealdehyde (961 mg, 5.49 mmol), the objective compound of (2) (the acetoacetic acid ester compound, 2.279 g, 4.99 mmol) and methyl 3-amino-crotonate (592 mg, 4.99 mmol) were added in a 50 ml-pear-shaped flask, whereto isopropanol (9 ml) was added. With a Dimroth condenser equipped on the flask, the mixture was stirred at 45° to 48° C. for 27.5 hours. The reaction solvent was distilled off under reduced pressure and the residue (3.714 g) was subjected to column chromatography [silica gel, chloroform-methanol (98.5:1.5)] and [silica gel, ethyl acetate-n-hexane (3:2)] for separation and purification to give 512 mg of the compound 6-1 (Yield: 13%).

$IR\nu_{max}^{KBr}cm^{-1}$: 1700(C=O)
$^1$H-NMRδ:
8.55–8.35 (1H),
7.95–7.75 (1H),
7.55–7.0 (11H),
7.0–6.6 (4H),
5.86 (1H, s),
5.59 (1H, s),
4.45–3.95 (3H),
3.57 (3H, s),
3.3–2.95 (4H),
2.95–2.6 (6H),
2.28, 2.24 (each 3H, s)

The compound 6-1 (473 mg. 0.665 mmol) was put in a 50 ml-pear-shaped flask, whereto ethanol (20 ml) was added to dissolve the content, and furmaric acid (77 mg, 0.665 mmol) was added. With an air condenser equipped on the flask, the mixture was stirred at room temperature for an hour. The reaction solvent was distilled off under reduced pressure to give about 550 mg of the compound.

$IR\nu_{max}^{KBr}cm^{-1}$: 3350(COOH),
2500(N$^+$H$^-$O$_2$C—)
1690(C=O)
$^1$H-NMRδ DMSO-d6+CDCl3(2:1.5):
8.67 (1H, s),
8.5–8.3 (1H),
8.0–7.8 (1H),
7.6–7.05 (11H),
7.05–6.65 (4H),
6.64 (2H, s),
5.45 (1H, s),
4.4–3.85 (3H),
3.48 (3H, s),
3.3–2.9 (4H),
2.9–2.3 (6H),
2.26, 2.20 (each 3H, s)

(6) 2-[4-(4-Benzhydrylpiperazino)phenyl] ethyl methyl 2,6-dimethyl-4-(3-nitrophenyl)-1,4-dihydropyridine-3,5-dicarboxylate (compound 7-1) and its monohydrochloride (compound 7-2)

In a 100 ml pear-shaped flask were put 3-nitrobenzaldehyde (1.144 g, 7.57 mmol), the objective compound of (3) (3.464 g, 7.59 mmol) and methyl 3-amino-crotonate (873 mg, 7.58 mmol), whereto isopropanol (12 ml) was added. With a Dimroth condenser equipped on the flask, the mixture was refluxed for 16 hours. The reaction solvent was distilled off under reduced pressure, and the obtained residue was subjected to column chromatography [silica gel, chloroform-methanol (45:1)] and [silica gel, ethyl acetate-n-hexane (2:3)] for separation to give a crude product. The crude product was purified by HPLC to give 2.503 g of the compound 7-1 (Yield: 48%).

$IR\nu_{max}^{KBr}cm^{-1}$: 1680(C=O), 1520(NO$_2$),
$^1$H-NMRδ:
8.06 (1H, t, J=2Hz),
7.97 (1H, ddd, J=8;2;1Hz),
7.1–7.6 (12H),
7.03 (2H, d, J=8.6Hz),
6.80 (2H, d, J=8.6Hz),
6.02 (1H, s),
5.07 (1H, s),
4.26 (1H, s),
4.22 (2H, t, J=7Hz),
3.64 (3H, s),
3.15((4H, dd, J=5;4.7Hz),
2.81 (2H, t, J=7Hz),
2.55 (4H, dd, J=5;4.7Hz),
2.33, 2.28 (each 3H, s)

The compound 7-1 (2.124 g; 3.16 mmol) was put in a 200 ml pear-shaped flask, which was equipped with a septum rubber. In the flask, methylene chloride (100 ml) was added to dissolve the content, and a dioxane solution of hydrogen chloride (1.20N, 2.64 ml) was added. The mixture was stirred at room temperature for 30 minutes. The reaction solvent was evaporated off under reduced pressure to give about 2.22 g of the compound 7-2.

$IR\nu_{max}^{KBr}cm^{-1}$: 2450(→N$^+$H$^-$Cl), 1680(C=O), 1520(NO$_2$),
$^1$H-NMRδ DMSO-d6:
9.17 (1H, s),
8.1–7.9, 7.5–7.3 (14H),
7.08 (2H, d, J=8Hz),
6.85 (2H, d, J=8Hz),
5.73 (1H, d, J=9Hz),
4.97 (1H, s),
4.14 (2H, t, J=6Hz),
3.8–3.55 (7H),
3.23 (4H, brs),
2.77 (2H, t, J=6Hz),
2.30, 2.26 (each 3H, s)

EXAMPLE 4

(1) 3-[4-(4-benzhydrylpiperazino)phenyl]propanol

Using 3-(p-aminophenyl)propanol instead of 2-(p-aminophenyl)ethanol, there was obtained the objective compound in the same manner as in Example 3(1)(2).

$IR\nu_{max}^{CHCl_3}cm^{-1}$: 3600(OH)
$^1$H-NMRδ:
7.5–7.05 (10H), 7.05–6.85 (2H), 6.85–6.6 (2H),
4.19 (1H, s), 3.55 (2H, t, J=6Hz), 3.25–2.95 (4H),
2.75–2.35 (6H), 2.05–1.45 (2H)

(2) 3-[4-(4-benzhydrylpiperazino)phenyl]propyl acetoacetate

Using the objective compound of Example 4(1), there was obtained the objective compound in the same manner as in

EXAMPLE 3(2).

$IR\nu_{max}^{film}cm^{-1}$: 1740(C=O), 1720(C=O)
$^1$H-NMRδ:
7.6–7.1 (10H), 7.1–6.9 (2H), 6.9–6.65 (2H),
4.27 (1H, s), 4.12 (2H, t, J=6Hz), 3.42 (2H, s),
3.35–3.0 (4H), 2.8–2.4 (6H), 2.26 (3H, s), 2.1–1.6 (2H)

We claim:

1. A compound of the formula

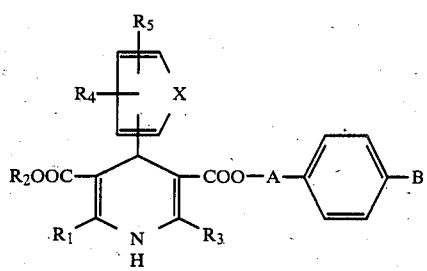

wherein each of $R_1$, $R_2$ and $R_3$ is, independently, lower alkyl, $C_{3-6}$ cycloalkyl or lower alkoxy lower alkyl;

each of $R_4$ and $R_5$ is, independently, a hydrogen atom, halogen, nitro, halogenated lower alkyl, lower alkylsulfonyl, halogenated lower alkoxy, lower alkylsulfinyl, lower alkyl, $C_{3-6}$ cycloalkyl, lower alkoxy, cyano, lower alkoxycarbonyl or lower alkylthio (wherein both $R_4$ and $R_5$ are not hydrogen atoms at the same time);

X is a group represented by vinylene or azomethine;
A is alkylene having from 2 to 4 carbon atoms;
B is $-N(R_6)_2$ or

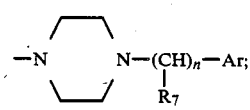

each of $R_6$ and $R_7$ is, independently, a hydrogen atom, lower alkyl, $C_{3-6}$ cycloalkyl, aralkyl (the alkyl of which has from 1 to 3 carbon atoms), phenyl, substituted phenyl, naphthyl, substituted napthyl (any substituent of substituted phenyl or of substituted naphthyl having one of the meanings of $R_4$), or pyridyl;

each of Ar and ar of aralkyl is phenyl, substituted phenyl, naphthyl, substituted naphthyl (any substitutent of substituted phenyl or of substituted naphthyl having one of the meanings of $R_4$) pyridyl and n is an integer from 0 to 2, inclusive. or an acid-addition salt thereof.

2. A compound as claimed in claim 1, wherein A is ethylene, or an acid-addition salt thereof.

3. A compound as claimed in claim 1, wherein X is azomethine, or an acid-addition salt thereof 4. A compound as claimed in claim 1, wherein X is vinylene, or an acid-addition salt thereof.

5. A compound as claimed in claim 1, wherein Ar is phenyl, or an acid-addition salt thereof.

6. A compound as claimed in claim 1, wherein $R_6$ is benzyl, or an acid-addition salt thereof.

7. A compound as claimed in claim 1, wherein $R_6$ is lower alkyl, or an acid-addition salt thereof.

8. A compound as claimed in claim 1, wherein both $R_7$ and Ar are phenyl and n is 1, or an acid-addition salt thereof.

9. A compound as claimed in claim 1, wherein Ar is phenyl, X is vinylene, A is ethylene and n is 0, or an acid-addition salt thereof.

10. A compound as claimed in claim 1, wherein each of $R_7$ and Ar is phenyl, X is vinylene, and n is 1, or an acid-addition salt thereof.

11. A compound as claimed in claim 1, wherein X is azomethine, $R_4$ or $R_5$ is trifluoromethyl or cyano, A is ethylene, and B is

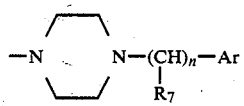

wherein each of $R_7$ and Ar is phenyl and n is (1), or an acid-addition salt thereof.

12. A compound as claimed in claim 1, wherein X is vinylene, $R_4$ or $R_5$ is nitro, A is ethylene, and B is

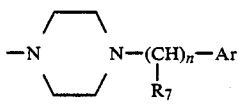

wherein, each of $R_7$ and Ar is phenyl, and n is (1), or an acid-addition salt thereof.

13. A compound as claimed in claim 1 wherein:
each alkyl has from 1 to 6 carbon atoms,
each cycloalkyl has from 3 to 6 ring carbon atoms,
each alkoxyalkyl has from 3 to 7 atoms,
each halogenated alkyl has from 1 to 4 carbon atoms,
each alkylsulfonyl has from 1 to 6 carbon atoms,
each halogenated alkoxy has from 1 to 3 carbon atoms,
each alkysulfinyl has from 1 to 6 carbon atoms,
each alkoxy has from 1 to 3 carbon atoms,
each alkoxycarbonyl has from 2 to 4 carbon atoms,
each alkylthio has from 1 to 3 carbon atoms,
each alkylene has from 2 to 4 carbon atoms,
the alkyl of each aralkyl has from 1 to 3 carbon atoms, and
each aryl and the ar of each aralkyl is phenyl or naphthyl.

14. A compound according to claim 1 which is pharmacologically acceptable and wherein each of Ar and ar of aralkyl is phenyl, naphthyl or pyridyl, and each phenyl or naphthyl is unsubstituted.

15. A pharmaceutical composition for prophylaxis or treatment of hypertension which comprises an effective amount of at least one compound as claimed in claim 1 or an acid-addition salt thereof, and pharmaceutically-acceptable additive.

* * * * *